(12) United States Patent
Lee et al.

(10) Patent No.: US 9,707,559 B2
(45) Date of Patent: Jul. 18, 2017

(54) BIOMATERIAL TEST APPARATUS AND METHOD OF CONTROLLING THE SAME

(71) Applicant: SAMSUNG ELECTRONICS CO., LTD., Suwon-si (KR)

(72) Inventors: Jung Tae Lee, Jeonju-si (KR); Chung Ung Kim, Yongin-si (KR); Jin Beom Hong, Seoul (KR); Jong Cheol Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/102,086

(22) PCT Filed: Nov. 21, 2014

(86) PCT No.: PCT/KR2014/011257
§ 371 (c)(1),
(2) Date: Jun. 6, 2016

(87) PCT Pub. No.: WO2015/083965
PCT Pub. Date: Jun. 11, 2015

(65) Prior Publication Data
US 2016/0325281 A1 Nov. 10, 2016

(30) Foreign Application Priority Data
Dec. 4, 2013 (KR) .................. 10-2013-0150158

(51) Int. Cl.
*G01N 35/00* (2006.01)
*G01N 30/30* (2006.01)
(Continued)

(52) U.S. Cl.
CPC ..... *B01L 3/502715* (2013.01); *B01L 3/50851* (2013.01); *B01L 7/00* (2013.01);
(Continued)

(58) Field of Classification Search
CPC .......... B01L 7/52; B01L 7/54; B01L 2200/10; B01L 3/502715; B01L 2400/0409;
(Continued)

(56) References Cited

U.S. PATENT DOCUMENTS

2005/0247701 A1\* 11/2005 Deka .................. B01L 7/52
219/548
2006/0275896 A1\* 12/2006 Anderson ............. C12M 23/22
435/303.1

(Continued)

*Primary Examiner* — Jennifer Wecker
(74) *Attorney, Agent, or Firm* — Sughrue Mion, PLLC

(57) ABSTRACT

Disclosed herein are a biomaterial test apparatus and a method of controlling the same, capable of previously sensing an ambient air temperature where a biomaterial test is performed in order to determine whether to proceed with the biomaterial test. The biomaterial test apparatus includes a housing, a platform receiving chamber arranged inside the housing and capable of receiving a platform into which a biomaterial is injected, a display which is arranged outside the housing and displays a control screen to test the biomaterial, a temperature sensor which senses a temperature of the platform receiving chamber and an air temperature in the vicinity thereof, and a control unit which, when the air temperature is less than a predetermined first critical temperature, controls the display so as to display a screen indicating that the test is impracticable.

18 Claims, 6 Drawing Sheets

(51) Int. Cl.
*G05D 23/19* (2006.01)
*B01L 3/00* (2006.01)
*B01L 7/00* (2006.01)
*C12M 1/36* (2006.01)
*C12Q 1/68* (2006.01)

(52) U.S. Cl.
CPC ............... *B01L 7/52* (2013.01); *G01N 30/30* (2013.01); *G01N 35/00069* (2013.01); *G01N 35/00722* (2013.01); *B01L 3/5027* (2013.01); *B01L 7/54* (2013.01); *B01L 2200/10* (2013.01); *B01L 2200/147* (2013.01); *B01L 2300/02* (2013.01); *B01L 2300/0803* (2013.01); *B01L 2300/18* (2013.01); *B01L 2300/1822* (2013.01); *B01L 2300/1861* (2013.01); *B01L 2300/1894* (2013.01); *B01L 2400/0409* (2013.01); *C12Q 1/686* (2013.01); *G01N 2030/3015* (2013.01); *G01N 2035/00346* (2013.01); *G01N 2035/00356* (2013.01); *G01N 2035/00366* (2013.01); *G01N 2035/00445* (2013.01); *G01N 2035/00891* (2013.01)

(58) Field of Classification Search
CPC ........... B01L 3/50851; B01L 2200/147; C12Q 1/686; G01N 2035/00346; G01N 2035/00366; G01N 2030/3015; G01N 30/30
See application file for complete search history.

(56) References Cited

U.S. PATENT DOCUMENTS

| | | | |
|---|---|---|---|
| 2009/0022625 A1* | 1/2009 | Lee | B01L 7/52 422/68.1 |
| 2011/0207209 A1* | 8/2011 | Hammons | C12M 23/42 435/297.1 |
| 2012/0052560 A1* | 3/2012 | Knight | B01L 3/502784 435/286.1 |

* cited by examiner

103

103

103

103

103

BIOMATERIAL TEST APPARATUS AND METHOD OF CONTROLLING THE SAME

CROSS-REFERENCE TO RELATED APPLICATION

This application is a National Stage entry of International Application No. PCT/KR2014/011257 filed Nov. 21, 2014, which claims priority from Korean Patent Application No. 10-2013-0150158 filed Dec. 4, 2013, the contents of all of which are incorporated herein by reference in their entirety.

TECHNICAL FIELD

The present invention relates to a biomaterial test apparatus which tests a biomaterial such as blood extracted from an object, and a method of controlling the same.

BACKGROUND ART

In recent years, a test apparatus using a micro-fluidic structure has been technically developed to diagnose specific diseases or determine whether or not a specific component is present, using a biomaterial such as a small quantity of blood or urine.

Such a test apparatus typically includes a chamber which may receive a biomaterial or reagent in the form of fluid, a channel in which a fluid may flow, and a valve which regulates the flow of a fluid. An apparatus manufactured to be capable of testing a biomaterial on a small disc is referred to as a bio disc. In particular, an apparatus manufactured to be capable of treating and operating a fluid on one chip in several steps is referred to as a lab-on-a-disc.

Most reagents/specimens to test a biomaterial are cold-stored for activity retention and stability thereof. Therefore, the reagents/specimens are typically used after being left at room temperature prior to testing. Since the temperature of the specimen is a major factor affecting an antigen-antibody reaction, a substrate reaction, an enzyme reaction, etc., it is important to perform an immunity analysis test or a clinical chemistry test at a constant temperature in order to obtain reproducible results.

DISCLOSURE

Technical Problem

Therefore, it is an aspect of the present invention to provide a biomaterial test apparatus and a method of controlling the same, capable of previously sensing an ambient air temperature where a biomaterial test is performed in order to determine whether to proceed with the biomaterial test.

Solution to Problem

In accordance with one aspect of the present invention, a biomaterial test apparatus includes a housing, a platform receiving chamber arranged inside the housing and capable of receiving a platform into which a biomaterial is injected, a display which is arranged outside the housing and displays a control screen to test the biomaterial, a temperature sensor which senses a temperature of the platform receiving chamber and an air temperature in the vicinity thereof, and a control unit which, when the air temperature is less than a predetermined first critical temperature, controls the display so as to display a screen indicating that the test is impracticable.

The air temperature may be an air temperature outside the platform receiving chamber within the housing.

The platform receiving chamber may include a heater which heats the inside of the platform receiving chamber, and when the air temperature is less than the first critical temperature, the control unit may block driving of the heater.

The platform receiving chamber may include a heater which heats the inside of the platform receiving chamber, and when the air temperature is equal to or more than the first critical temperature, the control unit may control the heater such that the inside of the platform receiving chamber is heated based on the air temperature.

When the air temperature is present within a predetermined non-preheating range, the control unit may operate the heater until a temperature of the platform receiving chamber reaches a predetermined preheating standby temperature.

When the temperature of the platform receiving chamber reaches the preheating standby temperature by the heater, the display may display a screen indicating that the test apparatus is in a preheating standby state.

When the air temperature is present within a predetermined preheatable range, the control unit may operate the heater until a temperature of the platform receiving chamber reaches a predetermined target temperature.

The display may display a screen indicating that the test apparatus is in a preheating progress state during operation of the heater, and when the temperature of the platform receiving chamber reaches the target temperature by the heater, the display may display a screen indicating that the test apparatus is in a preheating completion state or a testable state.

The platform receiving chamber may include a cooler to cool the inside of the platform receiving chamber.

When the air temperature exceeds a predetermined second critical temperature, the control unit may control the cooler so as to cool the inside of the platform receiving chamber.

In accordance with another aspect of the present invention, a method of controlling a biomaterial test apparatus including a platform receiving chamber arranged inside a housing and capable of receiving a platform into which a biomaterial is injected, includes identifying an air temperature in the vicinity thereof, comparing the air temperature with a predetermined first critical temperature, and displaying that a biomaterial test apparatus is impracticable on a display screen when the air temperature is less than a predetermined first critical temperature.

The air temperature may be an air temperature outside the platform receiving chamber within the housing.

The method may further include, when the air temperature is less than a predetermined first critical temperature, blocking driving of a heater which heats the inside of the platform receiving chamber.

The method may further include determining, when the air temperature is equal to or more than the first critical temperature, whether the air temperature is present within a predetermined preheatable range or a predetermined non-preheating range, and heating the inside of the platform receiving chamber based on the determined result.

When the air temperature is present in the non-preheating range, the inside of the platform receiving chamber may be heated until reaching a predetermined preheating standby temperature.

The method may further include, when the inside of the platform receiving chamber is heated and reaches the preheating standby temperature, displaying that the biomaterial test apparatus is in a preheating standby state on the display screen.

When the air temperature is present in the preheatable range, the inside of the platform receiving chamber may be heated until reaching a target temperature.

The method may further include displaying that the biomaterial test apparatus is in a preheating progress state on the display screen during heating of the platform receiving chamber, and displaying that the biomaterial test apparatus is in a preheating completion state or a testable state on the screen when the platform receiving chamber reaches the target temperature.

The method may further include cooling the platform receiving chamber when the air temperature exceeds the second critical temperature.

Advantageous Effects of Invention

In accordance with one aspect of a biomaterial test apparatus and a method of controlling the same, it may be possible to previously sense an ambient air temperature where a biomaterial test is performed and determine whether to proceed with the biomaterial test so that unnecessary preheating may be previously avoided. Thus, it may be possible to prevent waste of power and time due to preheating. In addition, since unnecessary preheating processes are reduced, a lifespan of a heater may be extended.

In accordance with another aspect of a biomaterial test apparatus and a method of controlling the same, it may be possible to previously sense an ambient air temperature where a biomaterial test is performed and control the test such that the test is performed only at an optimal temperature. As a result, it may be possible to enhance test reliability.

BRIEF DESCRIPTION OF DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1A:
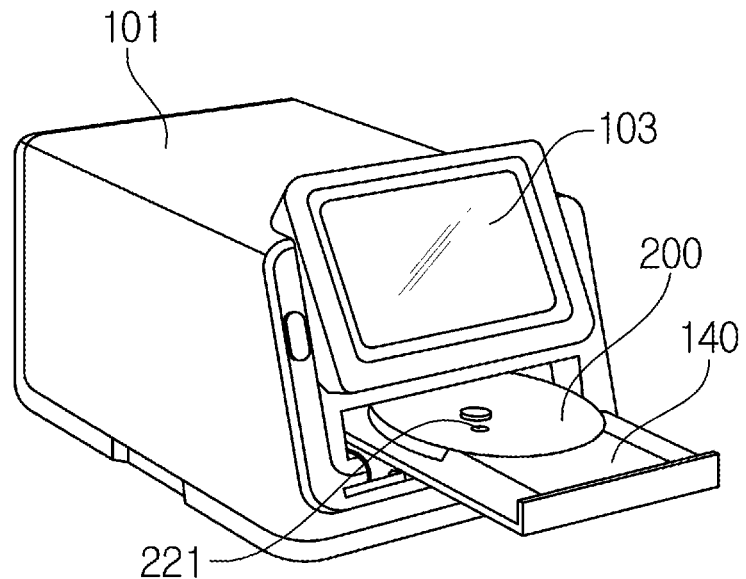
FIGS. 1A and 1B are views illustrating an external appearance of a biomaterial test apparatus according to an embodiment of the present invention.

Reference will now be made in detail to the embodiments of the present invention, examples of which are illustrated in the accompanying drawings, wherein like reference numerals refer to like elements throughout.

Figure 1B:
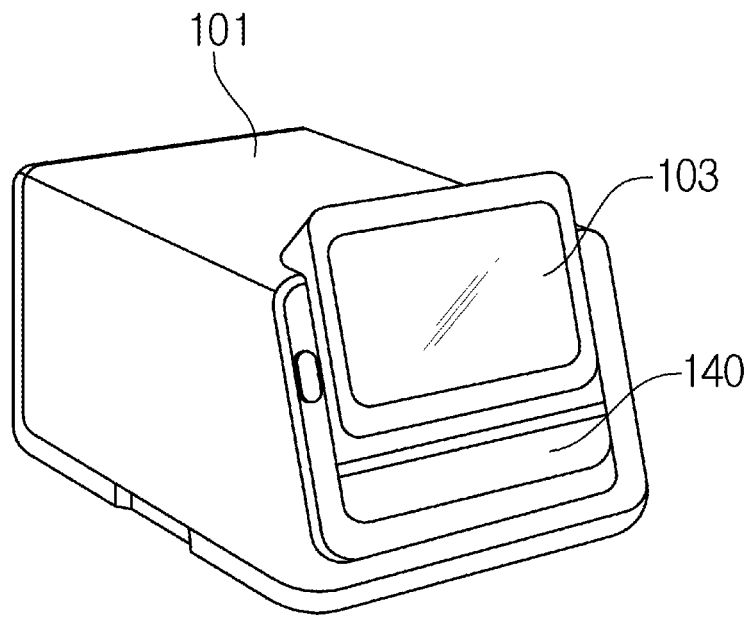

FIGS. 1A and 1B are views illustrating an external appearance of a biomaterial test apparatus according to an embodiment of the present invention.

Referring to FIGS. 1A and 1B, a biomaterial test apparatus 100 includes a tray 140 which may be inserted thereinto and ejected therefrom. A user injects a biomaterial sample through an inlet 221 provided on a platform 200 and places the platform 200 receiving the biomaterial sample on the tray 140. When the platform 200 is placed on the tray 140, the tray 140 is inserted into the biomaterial test apparatus 100.

The biomaterial test apparatus 100 displays a current state thereof and a test result or a control screen including a menu related to control thereof through the display 103 so that a user may input control commands. To this end, the biomaterial test apparatus 100 may also include a separate input portion, or the display 103 may also be embodied as a touchscreen or touch panel so as to function as an input portion.

For example, when a user inputs a control command related to ejection of the tray 140 through the input portion, the tray 140 is ejected as shown in FIG. 1A. When a user inputs a control command related to insertion of the tray 140 through the input portion or pushes the tray 140, the platform 200 is transported to the inside of the biomaterial test apparatus 100 while the tray 140 is inserted as shown in FIG. 1B.

Figure 2:
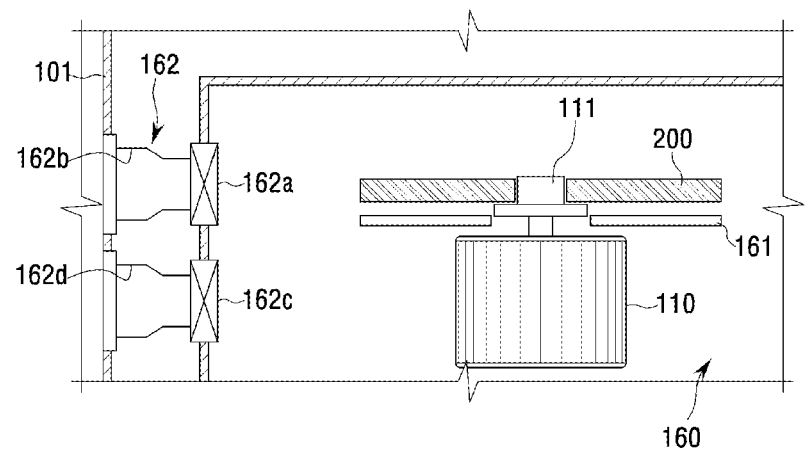
FIG. 2 is a side cross-sectional view illustrating the biomaterial test apparatus according to the embodiment of the present invention.
Figure 3:
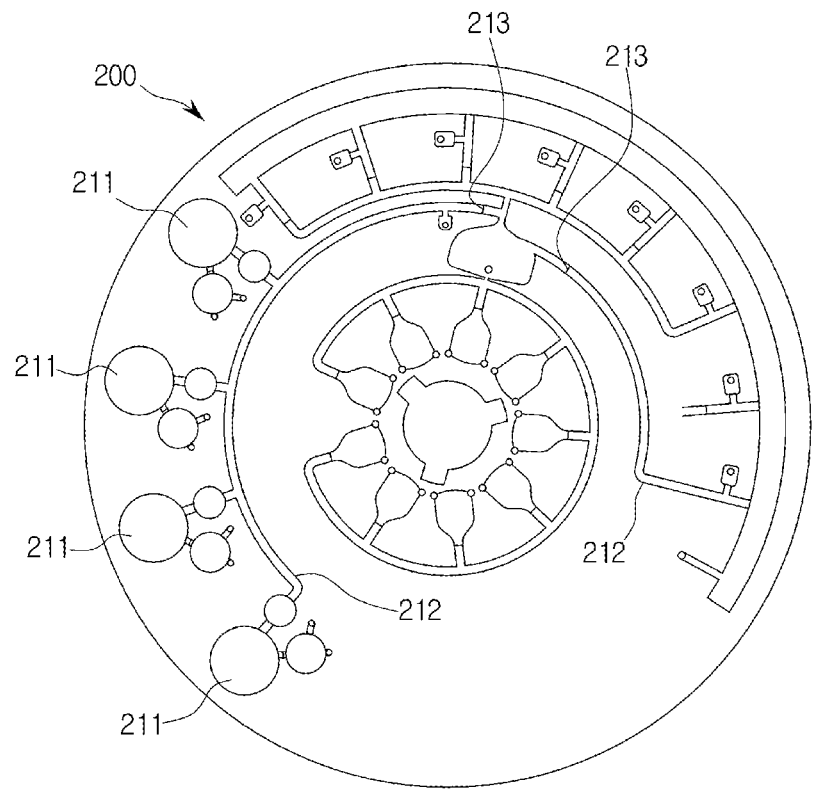
FIG. 3 is a top view illustrating a platform having a micro-fluidic structure in the biomaterial test apparatus according to the embodiment of the present invention.

FIG. 2 is a side cross-sectional view illustrating the biomaterial test apparatus according to the embodiment of the present invention. FIG. 3 is a top view illustrating the platform having a micro-fluidic structure in the biomaterial test apparatus according to the embodiment of the present invention.

Referring to FIG. 2, the biomaterial test apparatus 100 according to the embodiment of the present invention includes a platform receiving chamber 160 capable of receiving the platform 20 inside the a housing 101. The platform receiving chamber 160 may include a drive portion 110 which rotates the platform 200 when the platform is received therein, a heater 161 which heats the platform 200 or the inside of the platform receiving chamber 160, and a cooler 162 which cools the same.

A hole is provided at a center of the platform 200 capable of being received in the platform receiving chamber 160. A turntable 111, which supports and rotates the platform 200, is inserted into the hole and the drive portion 110 applies rotation power to the turntable 111 to rotate the platform 200. The drive portion 110 may be a drive motor.

Referring to FIG. 3, the platform 200 includes a micro-fluidic structure in which a specific reaction may be performed using a biomaterial such as blood as a specimen. The micro-fluidic structure includes a variety of chambers 211 each of which receives a fluid such as a bio-specimen or a reagent such that a reaction between the specimen and the reagent is generated and detected in the chamber, at least one channel 212 which connects between the chambers, and at least one valve 213 which controls opening and closing of the channel.

The fluid is transferred through the channel 212 between the chambers in the platform 200 by centrifugal force generated by rotation of the platform 200. In a case in which the bio-specimen is blood, the centrifugal force separates serum from the blood.

The heater 161 may be configured of various types of heaters such as a resistor and a halogen lamp. Although the heater 161 is arranged at a lower portion of the platform receiving chamber 160 in the embodiment of FIG. 2, the heater 161 may also be arranged at an upper portion of the platform receiving chamber 160 for more efficient heating.

The cooler 162 may include an inlet fan 162*a* by which outdoor air is forcibly introduced into the platform receiving chamber 160 and an intake duct 162*b* through which outdoor air is guided inside the platform receiving chamber 160. In addition, the cooler 162 may include an outlet fan 162*c* by which indoor air in the platform receiving chamber 160 is forcibly discharged to the outside and an exhaust duct 162*d* through which the indoor air is guided to the outside.

Although the cooler 162 is embodied as a fan in the embodiment of FIG. 2, the present invention is not limited thereto. For example, in other embodiments, a thermoelectric cooler may also be provided in the platform receiving chamber 160, and any configuration is applicable so long as air may be cooled in the platform receiving chamber 160.

Figure 4:
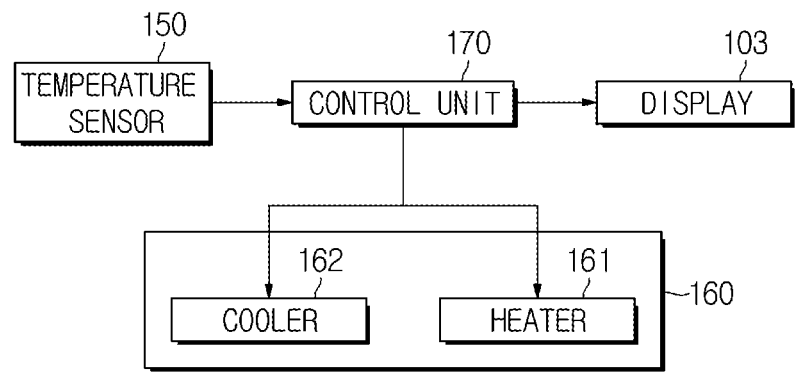
FIG. 4 is a control block diagram of the biomaterial test apparatus according to the embodiment of the present invention.

FIG. 4 is a control block diagram of the biomaterial test apparatus according to the embodiment of the present invention.

As shown in FIG. 4, the biomaterial test apparatus according to the embodiment includes the platform receiving chamber 160 which is provided inside the housing 101 and is capable of receiving the platform to perform various tests of a biomaterial, the display 103 which displays a control screen to control the test of a biomaterial when the platform is received in the platform receiving chamber, a temperature sensor 150 which senses a temperature in the housing 101, and a control unit 170 which controls the display so as to display a screen indicating that the test is impracticable when the temperature sensed by the temperature sensor is less than a first critical temperature.

In addition, in accordance with the biomaterial test apparatus according to the embodiment, the platform receiving chamber 160 may include the heater 161 which heats the inside of the platform receiving chamber 160 or the cooler 162 which cools the inside of the platform receiving chamber 160.

As described above, the platform 200 received in the platform receiving chamber 160 includes the micro-fluidic structure so as to test a biomaterial such as blood. The platform 200 mainly has a disc shape, but the present invention is not limited thereto. For example, the platform 200 may also have a fan shape so as to be seated on a rotatable frame and be rotatable, as well as a complete disc shape so as to be rotatable in itself.

The platform 200 may be easily formed and the surface thereof may be made of a bio-inactive plastic material such as PMMA, PDMS, or PC. Furthermore, any material is applicable to the platform so long as it has chemical and biological stability, optical transparency, and mechinability.

Although the drive portion 110 may be embodied as a motor as described above, any configuration is applicable so long as driving force may be provided and rotate the platform 200. When the drive portion 110 rotates the platform 200, fluid specimens are transferred by centrifugal force and testing begins.

As described above, a biomaterial such as blood should be tested at a proper temperature in order to obtain an accurate test result. A reaction using a biomaterial generally indicates an optimal reaction result at about 37° C. similar to the normal temperature of the human body. However, a user may set a target temperature for a proper test according to test materials or test types. When the target temperature is set, a temperature of the platform receiving chamber 160 is adjusted to the target temperature so that a biomaterial may be tested in an optimal environment.

The platform receiving chamber 160 may include the heater 161 or the cooler 162 as described above. Since the temperature of the platform receiving chamber 160 is generally lower than the target temperature, the heater 161 may heat the inside of the platform receiving chamber 160. When the inside of the platform receiving chamber 160 is heated and reaches the target temperature, the heater 161 stops heating such that the biomaterial test may proceed. If the temperature of the platform receiving chamber 160 is higher than the target temperature, the inside of the platform receiving chamber 160 may be cooled by the cooler 162 so as to reach the target temperature.

However, even when the target temperature is set and the inside of the platform receiving chamber 160 is heated or cooled, the inside of the platform receiving chamber 160 may not reach the target temperature. Therefore, in order to control the inside of the platform receiving chamber 160 at a proper temperature, the biomaterial test apparatus has to be placed in a proper temperature environment.

For example, in a case in which the biomaterial test apparatus is placed in an environment less than 0° C., even when the inside of the platform receiving chamber 160 is heated for a typical preheating time of 30 minutes, the inside of the platform receiving chamber 160 may not reach the typical target temperature of 37° C. Accordingly, when a preheating process is performed regardless of temperature of the environment in which the biomaterial test apparatus is placed, unnecessary time may be wasted. Particularly, if an emergency patient waits for a preheating time but does not undergo testing, it is difficult to take rapid emergency measures. In addition, since the heater 161 is unnecessarily operated, a lifespan of the heater 161 may be shortened. Moreover, since the platform 200, into which a biomaterial is injected, is inserted into the biomaterial test apparatus in order to determine whether or not to proceed with the test, the platform 200 including the biomaterial may be wasted.

Accordingly, there is a need to identify an environment in which the biomaterial test apparatus is placed before preheating of the platform 200 is performed so as to previously inform a tester whether to proceed with the preheating.

The temperature sensor 150 may identify an environment in which the biomaterial test apparatus is placed, specifically a temperature of the platform receiving chamber 160 where preheating is performed and an ambient air temperature thereof.

Here, the ambient region of the platform receiving chamber may mean a region adjacent to an outer surface of the platform receiving chamber. Particularly, the ambient region of the platform receiving chamber may mean an outer region of the platform receiving chamber within the housing. However, the present invention is not limited to this embodiment and may also include a region adjacent to the outside of the housing when the platform receiving chamber is close to the housing. That is, the ambient region of the platform receiving chamber may include a region having an effect that the inside of the platform receiving chamber reaches a target temperature.

Figure 5A:
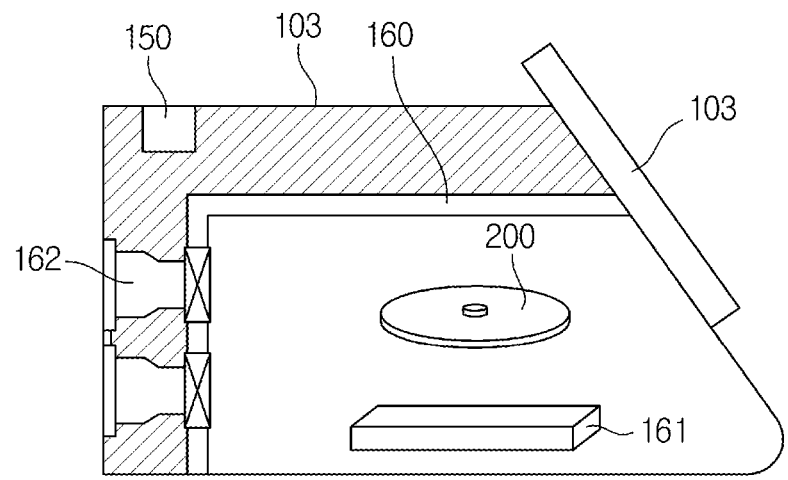
FIG. 5A is a view illustrating a temperature sensor which senses a temperature in a platform receiving chamber and an air temperature in the vicinity thereof before the platform is inserted into the platform receiving chamber.

FIG. 5A is a view illustrating the temperature sensor which senses a temperature of the platform receiving chamber and an air temperature in the vicinity thereof before the platform is inserted into the platform receiving chamber. As shown in FIG. 5A, the temperature sensor 150 may be arranged inside the housing 101. On the other hand, the temperature sensor 150 may also be arranged outside the housing 101.

The temperature sensor 150 is a contact temperature sensor. The temperature sensor 150 may include a glass temperature sensor, a bimetal temperature sensor, a resistance temperature detector, a thermocouple temperature sensor, a thermistor, and the like, but the present invention is not limited thereto. For example, any configuration is applicable so long as a sensing unit may sense an air temperature in the vicinity of the platform receiving chamber 160.

Referring to FIG. 5A, the temperature sensor 150 may sense an air temperature of a hatched region. That is, the air temperature in the vicinity of the platform receiving chamber 160 may mean an air temperature outside the platform receiving chamber 160 within the housing 101. Since the air temperature in this region comes into direct contact with the platform receiving chamber 160, the air temperature may have an effect to heat the inside of the platform receiving chamber 160. Accordingly, the temperature sensor 150 may sense an air temperature of the hatched region in FIG. 5A before preheating of the platform 200 so as to thus determine whether to proceed with the biomaterial test.

Figure 5B:
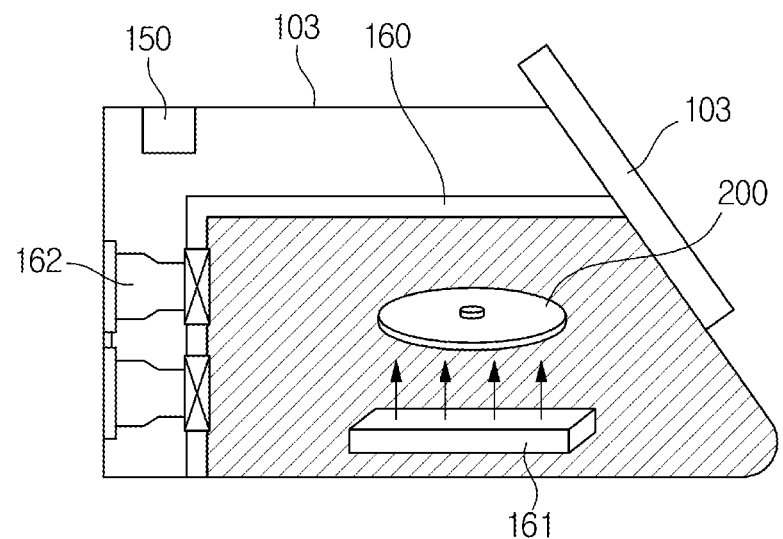
FIG. 5B is a view illustrating a heater to heat the inside of the platform receiving chamber.

For example, if the sensed air temperature is determined to be a temperature suitable to proceed with the biomaterial test, platform preheating may be performed. As shown in FIG. 5B, when the platform 200 is received in the platform receiving chamber 160, the heater 161 in the platform receiving chamber 160 heats the inside of the platform receiving chamber 160 so that preheating of the platform 200 may be performed. Here, the inside of the platform receiving chamber 160 may mean a hatched region of FIG. 5B.

When the temperature sensor 150 senses the air temperature as described above, the following operations may be determined according to the sensed result. Hereinafter, an operation of the control unit 170 will be described based on the result of the air temperature sensed by the temperature sensor 150.

The control unit 170 may control processes of the biomaterial test based on the air temperature sensed by the temperature sensor 150. Specifically, the control unit 170 compares the air temperature sensed by the temperature sensor 150 with a predetermined first critical temperature so as to determine whether to proceed with the biomaterial test.

As described above, in a case in which the biomaterial test apparatus is placed in an extremely low temperature environment, even when the platform 200 is preheated for a sufficient time, the platform 200 may not reach a desired temperature. Accordingly, in order to previously block an unnecessary preheating operation, the first critical temperature may be previously set so as to determine whether or not the biomaterial test apparatus is placed at an extremely low temperature state. This may also be input through the input portion by a tester or may also be determined by calculation within the biomaterial test apparatus.

The control unit 170 determines whether the air temperature sensed by the temperature sensor 150 is less than the first critical temperature. If the air temperature in the vicinity of the platform receiving chamber 160 is less than the first critical temperature, the control unit 170 may control the screen of the display 103 so as to inform a tester that the biomaterial test is impracticable. In addition, the control unit 170 may block the operation of the heater 161 so as to prevent waste of unnecessary power and time.

For example, when a tester sets 0° C. to the first critical temperature, the control unit 170 determines whether the air temperature sensed by the temperature sensor 150 is less than 0° C. If the air temperature in the vicinity of the platform receiving chamber 160 is less than 0° C., the control unit 170 informs a tester that the biomaterial test is impracticable and may control the heater 161 so that the heater 161 is not operated.

In addition, if the air temperature sensed by the temperature sensor 150 is equal to or more than the first critical temperature, the control unit 170 may control the heater 161 such that preheating of the platform 200 is performed.

Specifically, it may be possible to previously set a non-preheating range and a preheatable range in a temperature equal to or more than the first critical temperature. Here, the non-preheating range means an air temperature range in which the temperature of the platform receiving chamber 160 may not reach a target temperature even when the platform receiving chamber 160 is heated in a temperature equal to or more than the first critical temperature. In addition, the preheatable range means an air temperature range in which the temperature of the platform receiving chamber 160 may reach a target temperature when the platform receiving chamber 160 is heated in a temperature equal to or more than the first critical temperature. The preheatable range and the non-preheating range may also be input through the input portion by a tester or may also be determined by calculation within the biomaterial test apparatus.

The air temperature present in the non-preheating range may be always lower than the air temperature present in the preheatable range.

When the non-preheating range and the preheatable range are set, the control unit 170 determines whether the air temperature sensed by the temperature sensor 150 is present in any of the non-preheating range and the preheatable range. When the non-preheating range does not overlap with the preheatable range, a case in which the air temperature is simultaneously present in the two ranges is not generated. However, a case in which the air temperature is not simultaneously present in the two ranges may also be generated.

If the air temperature is present in the preheatable range, the control unit 170 allows the biomaterial test to be performed in an optimal environment by execution of preheating. That is, the heater 161 may be operated until the inside of the platform receiving chamber 160 reaches a predetermined target temperature. In this case, the target temperature means an optimal temperature to perform the biomaterial test, and may be input by a tester or may be determined by calculation within the apparatus.

For example, the preheatable range may be set to 13° C. to 25° C. and the target temperature may be set to 37° C. When the air temperature sensed by the temperature sensor 150 is present in 13° C. to 25° C., the control unit 170 may operate the heater 161 so as to heat the inside of the platform receiving chamber 160. When the platform receiving chamber 160 reaches the target temperature of 37° C. by heating thereof, the control unit 170 stops the operation of the heater 161 such that the biomaterial test may be performed at an optimal temperature.

Since the temperature of the platform receiving chamber 160 reaches 37° C. without preheating, the temperature of 25° C. to 37° C. is excluded in the above example. When the platform 200 is inserted into the platform receiving chamber 160, the biomaterial test is prepared. Due to heat generated in this case, the platform receiving chamber 160 naturally reaches the target temperature of 37° C. However, since the above-mentioned example is merely an embodiment of the biomaterial test apparatus, the preheatable range may be freely set so long as the temperature of the platform receiving chamber 160 reaches the target temperature of 37° C.

Meanwhile, when the air temperature is present in the non-preheating range, the inside of the platform receiving chamber 160 may not reach the target temperature even during preheating. In this case, performing the preheating may cause waste of power and time. However, when the biomaterial test apparatus moves from a low temperature environment to an air temperature environment within the preheatable range, the inside of the platform receiving chamber 160 may reach the target temperature through preheating.

Accordingly, the control unit 170 may operate the heater 161 until the inside of the platform receiving chamber 160 only reaches a preset heating standby temperature. When the inside of the platform receiving chamber 160 reaches the heating standby temperature, the state after that time is a preheating standby state. When the air temperature is present in the preheatable range for the future, preheating may be performed.

For example, the non-preheating range may be set to 0° C. to 13° C. and the preheating standby temperature may be set to 10° C. In a case in which the air temperature sensed by the temperature sensor 150 is present in 0° C. to 13° C., the inside of the platform receiving chamber 160 may not reach a target temperature even when being heated using the heater 161. Accordingly, the control unit 170 does not operate the heater 161 until the inside of the platform receiving chamber 160 reaches the target temperature. Instead, the control unit 170 may operate the heater 161 until the inside of the platform receiving chamber 160 only reaches a preset heating standby temperature of 10° C. The preheating standby state is when the inside of the platform receiving chamber 160 reaches 10° C. by the heater 161. The biomaterial test apparatus is not operated until the air temperature is present in the preheatable range in the preheating standby state. When the air temperature is present in the preheatable range or the biomaterial test apparatus moves to the air temperature environment within the preheatable range for the future, the control unit 170 may operate the heater 161 such that the temperature of the platform receiving chamber 160 reaches the target temperature.

Figure 6:
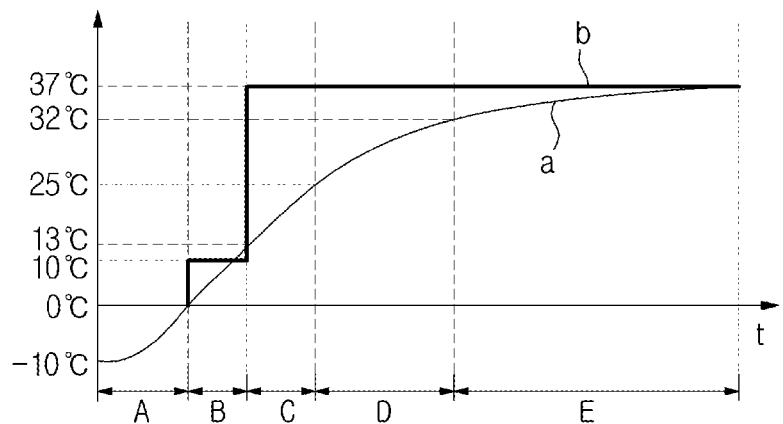
FIG. 6 is a graph illustrating a method of controlling a temperature of the platform receiving chamber in response to the air temperature according to the embodiment of the present invention.

FIG. 6 is a graph illustrating a method of controlling a temperature of the platform receiving chamber in response to the air temperature according to the embodiment of the present invention. In the graph, "a" refers to an air temperature in the vicinity of the platform receiving chamber, and "b" refers to a setting temperature to control a temperature of the platform receiving chamber in response to the air temperature. The X-axis refers to a time (t) and the Y-axis refers to a temperature.

Prior to controlling a temperature of the platform receiving chamber 160 by a method in FIG. 6, there is a need to set a first critical temperature, a target temperature, a preheatable range, a non-preheating range, and a preheating standby temperature so as to control the temperature of the platform receiving chamber 160 based on the same.

For example, the first critical temperature as the lowest temperature at which the biomaterial test apparatus may operate may be set to 0° C., the target temperature as a temperature of the platform receiving chamber 160 set to enable the biomaterial test apparatus to be performed in an optimal environment may be set to 37° C., the preheatable range as an air temperature range may reach the target temperature when the inside of the platform receiving chamber 160 is heated may be set to 13° C. to 25° C., the non-preheating range as an air temperature range may not reach the target temperature even when the inside of the platform receiving chamber 160 is heated may be set to 0° C. to 13° C., and the preheating standby temperature as a temperature at which the inside of the platform receiving chamber 160 is set as the preheating standby state when the biomaterial test apparatus moves to the preheatable range for the future may be set to 10° C.

Referring to line "a" in the graph of FIG. 6, the graph may be divided into four sections according to the air temperature in the vicinity of the platform receiving chamber 160 so as to control the heater 161. First, "A" section means a case in which the air temperature is less than the first critical temperature of 0° C. As described above, when the air temperature is less than the first critical temperature, the inside of the platform receiving chamber 160 may not reach the target temperature of 37° C. even when being heated. Accordingly, the operation of the heater 161 may be blocked in order to prevent unnecessary waste of power. Line "b" is not indicated in the "A" section of FIG. 6. This case means that the inside of the platform receiving chamber 160 is not heated by blocking the operation of the heater 161.

"B" section means a case in which the air temperature is present in the non-preheating range of 0° C. to 13° C. This case means that the inside of the platform receiving chamber 160 may not reach the target temperature of 37° C. even when being heated. However, since the inside of the platform receiving chamber 160 may reach the target temperature according to an environment change for the future, the inside of the platform receiving chamber 160 may be adjusted to the preheating standby temperature of 10° C. Accordingly, as line "b" in the graph, the control unit 170 may set the temperature of the platform receiving chamber 160 to the preheating standby temperature of 10° C. and maintain the same.

"C" section means a case in which the air temperature is present in the preheatable range of 13° C. to 25° C. This case means that the inside of the platform receiving chamber 160 may reach the target temperature of 37° C. when being heated. Accordingly, as line "b" in the graph, the inside of the platform receiving chamber 160 may be controlled to reach the target temperature by setting the temperature of the platform receiving chamber 160 to the target temperature of 37° C. and driving the heater 161 in the "C" section.

"D" section means a case in which the air temperature is present in a temperature range of 25° C. to 32° C. and the inside of the platform receiving chamber 160 is not heated in the "D" section. Prior to performing the biomaterial test, a preparation process such as material separation is performed. Due to heat generated by this process, the temperature of the platform receiving chamber 160 may naturally reach the target temperature of 37° C. Accordingly, the temperature of the platform receiving chamber 160 is set to 37° C. as line "b" in the graph, but the heater 161 may not be separately driven. However, it is not that the heater 161 is not necessarily driven. For example, it may be possible to determine whether to operate the heater 161 such that the temperature of the platform receiving chamber 160 reaches a temperature of 37° C.

"E" section means a case in which the air temperature is present in a temperature range of 32° C. to 37° C. and the biomaterial test may be performed without the operation of the heater 161. When the temperature of the platform receiving chamber 160 exceeds the target temperature of 37° C. during testing, the temperature of the platform receiving chamber 160 may be maintained at the target temperature of 37° C. by the operation of the cooler 162.

The description is given that the control unit 170 controls the temperature of the platform receiving chamber 160 using the heater 161 until now. However, the control unit 170 may also control the temperature of the platform receiving chamber 160 using the cooler 162. Specifically, when the air temperature exceeds a predetermined second critical temperature, the control unit 170 may control the cooler 162 to cool the inside of the platform receiving chamber 160. Here, the second critical temperature may be higher than the first critical temperature.

For example, when the air temperature exceeds 32° C., the inside of the platform receiving chamber 160 may exceeds the target temperature of 37° C. in a preparation process before the biomaterial test. Therefore, 32° C. may be set as the second critical temperature. When the air temperature in the vicinity of the platform receiving chamber 160 sensed by the temperature sensor 150 exceeds the second critical temperature of 32° C., the control unit 170 may operate the cooler 162. When the temperature of the platform receiving chamber 160 is maintained at 37° C. by the cooler 162, the control unit 170 stops the operation of the cooler 162 and the biomaterial test begins.

In addition, the control unit 170 may control the temperature of the platform receiving chamber 160 and the screen displayed on the display 102, thereby assisting an external tester to identify that the biomaterial test apparatus is performed, which will be described later.

Again referring to FIG. 4, the temperature of the platform receiving chamber 160 may be controlled by the control unit 170. To this end, the platform receiving chamber 160 may include the heater 161 which heats the inside of the platform receiving chamber 160 and the cooler 162 which cools the inside of the platform receiving chamber 160.

The heater 161 may heat the inside of the platform receiving chamber 160 according to the air temperature in the vicinity of the platform receiving chamber 160. This may be controlled by the control unit 170. As described above, when the air temperature is less than the first critical temperature, the heater 161 is not operated to prevent waste of power and time. Meanwhile, when the air temperature is present in the preheatable range, the heater 161 may heat the inside of the platform receiving chamber 160 until the temperature of the platform receiving chamber 160 reaches the target temperature. However, when the air temperature is present in the non-preheating range, the heater 161 operates such that the inside of the platform receiving chamber 160 reaches the preheating standby temperature and the platform receiving chamber 160 enters the preheating standby state.

The cooler 162 may cool the inside of the platform receiving chamber 160 according to the air temperature in the vicinity of the platform receiving chamber 160. As described above, when the air temperature exceeds the second critical temperature, the cooler 162 may cool the inside of the platform receiving chamber 160 in order to provide an optimal test environment.

Again referring to FIG. 4, the display 103 may display the control screen to control the biomaterial test apparatus. Moreover, the display 103 may also display a progress state on the screen such that an external tester may identify an operation performed by the biomaterial test apparatus.

Figure 7:
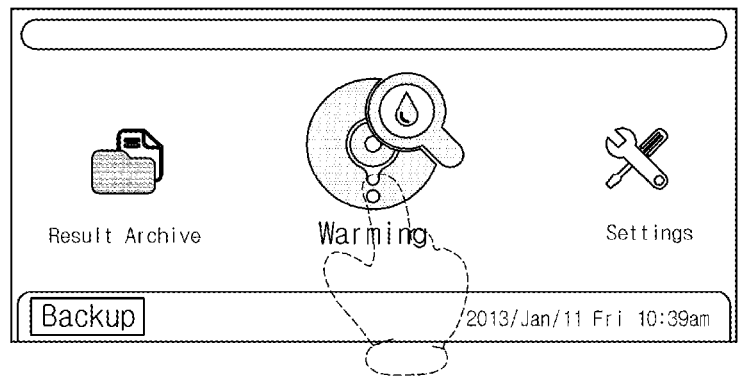
FIG. 7 is a view illustrating a display which displays a control screen according to the embodiment of the present invention.

FIG. 7 is a view illustrating the display which displays the control screen according to the embodiment of the present invention. When a left icon is activated in the screen, it may be possible to identify a biomaterial test result. A central icon may be an icon to proceed with the biomaterial test. In addition, when a right icon is activated, it may be possible to control detail settings of the biomaterial test apparatus.

The display 103 may inform an external tester that the biomaterial test apparatus is performed. Hereinafter, a description will be given of a method of informing the outside of the progress state of the biomaterial test apparatus through the central icon.

Figure 8A:
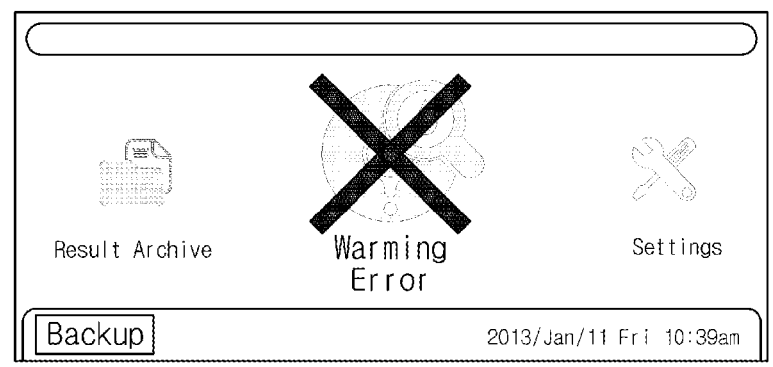
FIGS. 8A to 8D are views illustrating a screen which indicates an operation state of the biomaterial test apparatus according to the embodiment of the present invention.

FIG. 8A is a view illustrating an example of a screen which indicates an inoperative state of the biomaterial test apparatus.

When the air temperature sensed by the temperature sensor 150 is less than the first critical temperature, the biomaterial test apparatus may not normally perform the biomaterial test. Therefore, it may be impossible to obtain an exact result when the biomaterial test apparatus is performed in an extremely low temperature environment. In addition, the inside of the platform receiving chamber 160 may not reach a target temperature even when being heated to provide a proper temperature environment.

Thus, there is a need to previously inform an external tester of such a state before preheating for testing is performed. When the air temperature sensed by the temperature sensor 150 is less than the first critical temperature, the display 103 may display a screen indicating that the test is impracticable according to a command of the control unit 170 as shown in FIG. 8A. The tester identifies the above state such that the unnecessary preheating and testing are not performed, and thus it may be possible to prevent waste of power and time.

In addition, when the display 103 displays the screen as shown in FIG. 8A, the central icon may be not activated any more. In this case, the biomaterial test may be again performed only when the biomaterial test apparatus is rebooted.

Figure 8B:
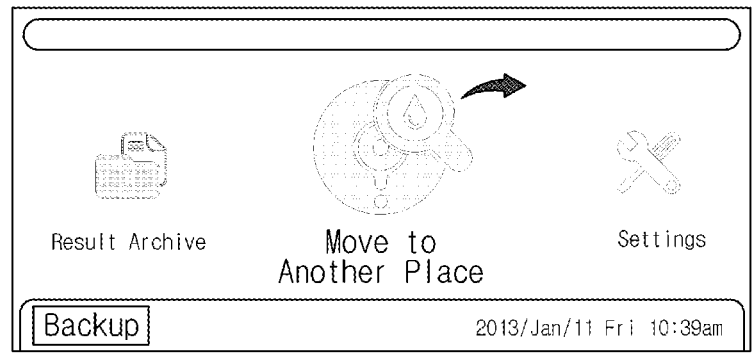

FIG. 8B is a view illustrating an example of a screen which indicates that the biomaterial test apparatus is in a preheating standby state.

When the air temperature sensed by the temperature sensor 150 is present in a non-preheating range, the inside of the platform receiving chamber 160 may not reach the target temperature even when being heated. Accordingly, the temperature of the platform receiving chamber 160 is adjusted to a preheating standby temperature so as to enter a preheating standby state. The preheating standby state means a state in which the temperature of the platform receiving chamber 160 may be maintained to the preheating standby temperature and preheating may be performed when the air temperature in the vicinity of the platform receiving chamber 160 is increased to a temperature capable of being preheated for the future.

Accordingly, when the air temperature is present in the non-preheating range, there is a need to inform an external tester that the biomaterial test apparatus is in the preheating standby state. As shown in FIG. 8B, the display 103 informs the tester that the biomaterial test apparatus in the preheating standby state moves to another place so as to perform testing. When the tester identifies that the biomaterial test apparatus is in the preheating standby state through the display 103, the tester may move the biomaterial test apparatus to an air temperature present in the preheatable range so as to perform preheating.

Unlike the inoperative screen of FIG. 8A, the central icon may be activated according to a change in air temperature for the future even when the preheating standby screen of FIG. 8B is displayed. That is, when the air temperature is present in the preheatable range by movement of place for the future, the deactivated central icon is reactivated so that the biomaterial test apparatus may be performed.

Figure 8C:
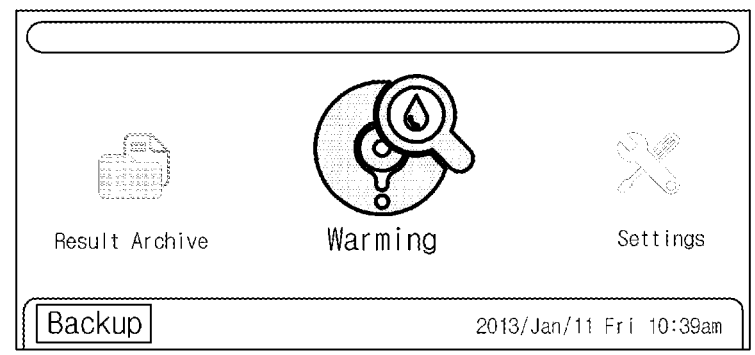

FIG. 8C is a view illustrating an example of a screen which indicates that the biomaterial test apparatus is in a preheating progress state.

When the air temperature sensed by the temperature sensor 150 is present in a preheatable range, the control unit 170 controls the heater 161 such that the inside of the platform receiving chamber 160 is heated. Accordingly, there is a need to inform an external tester that the inside of the platform receiving chamber 160 is heated in the biomaterial test apparatus. As shown in FIG. 8C, the display 103 may inform the external tester of a preheating progress state, thereby enabling the biomaterial test to be prepared to be performed by the tester.

Figure 8D:
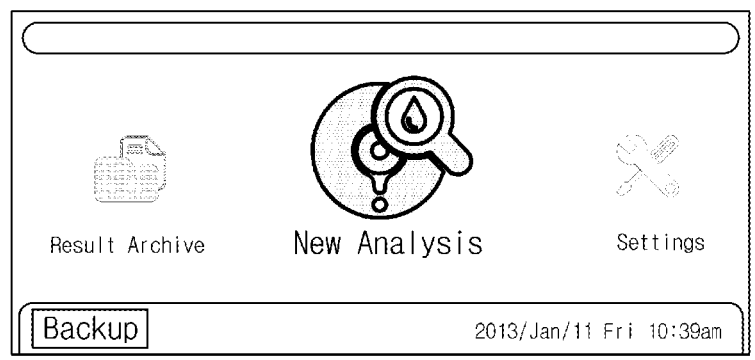

FIG. 8D is a view illustrating an example of a screen which indicates that the biomaterial test apparatus is in a testable state.

When the inside of the platform receiving chamber 160 is heated and reaches a target temperature, the biomaterial test may be performed in an optimal environment to proceed therewith. The display 103 may display the preheating progress state as shown in FIG. 8C when preheating is performed. Subsequently, the display 103 may display the testable state as shown in FIG. 8D when preheating is completed. When the external tester identifies the testable state through the display 103, a biomaterial injected into the platform 200 may be tested.

FIG. 8D illustrates a case in which the display 103 displays the screen indicating the testable state when preheating is completed. However, the display 103 may also display a screen indicating that the biomaterial test apparatus is in a preheating completion state.

The progress state of the biomaterial test may be displayed through the display 103 according to the air temperature in the vicinity of the platform receiving chamber 160 sensed by the temperature sensor 150. Therefore, the external tester may determine whether the air temperature in the vicinity of the platform receiving chamber 160 is in a proper environment to proceed with the biomaterial test so as to thus take proper measures.

The screens shown in FIGS. 8A to 8D according to the operation of the biomaterial test apparatus are arranged as indicated by Table 1. In Table 1, the first critical temperature is assumed as 0° C., the target temperature is assumed as 37° C., the preheatable range is assumed as 13° C. to 25° C., the non-preheating range is assumed as 0° C. to 13° C., and the preheating standby temperature is assumed as 10° C. In Table 1, $t_0$ refers to the air temperature in the vicinity of the platform receiving chamber 160.

TABLE 1

| Temperature | Operation | Display screen | Note |
|---|---|---|---|
| $t_0 < 0°$ C. | Blocking heater operation | FIG. 8A | Return when power is turned ON/OFF |
| $0°$ C. $\leq t_0 < 13°$ C. | Heater operation until temperature in chamber reaches 10° C. | FIG. 8B | Automatic return |
| $13°$ C. $\leq t_0 < 25°$ C. | Heater operation until temperature in chamber reaches 37° C. | FIG. 8C | Automatic return |
| $25°$ C. $\leq t_0 < 32°$ C. | Test standby | FIG. 8D | Automatic return |

Referring to Table 1, when the air temperature is less than the first critical temperature of 0° C., the operation of the heater 161 is blocked in the biomaterial test apparatus and the screen indicating that the test is impracticable is displayed as shown in FIG. 8A. When the air temperature is present in the non-preheating range, the heater 161 is operated until the temperature in the chamber reaches the preheating standby temperature of 10° C. and the screen indicating the preheating standby state is displayed as shown in FIG. 8B. When the air temperature is present in the preheatable range, the heater 161 is operated until the temperature in the chamber reaches the target temperature of 37° C. In addition, the screen indicating the preheating progress state is displayed as shown in FIG. 8C during the operation of the heater 161. When the temperature in the chamber reaches the target temperature of 37° C., the screen indicating the test standby state is displayed as shown in FIG. 8D.

Meanwhile, as indicated by Table 1, when the air temperature is less than the first critical temperature, the apparatus has to be rebooted by turning on power so as to be operated, but otherwise the screens of FIGS. 8B to 8D may be automatically switched or returned according to progress thereof.

Figure 9:
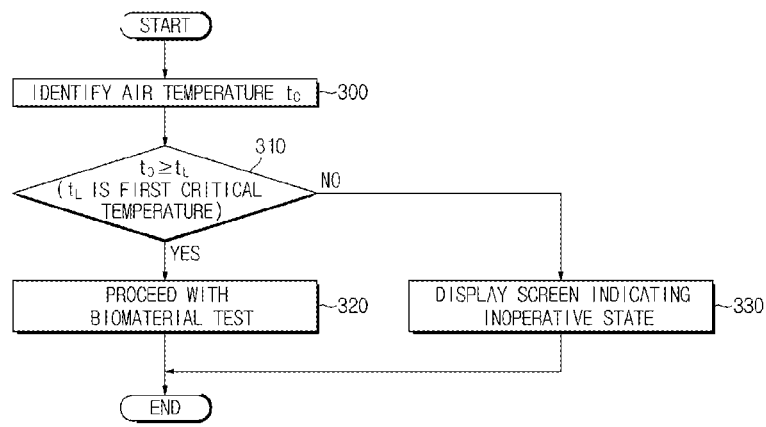
FIG. 9 is a flowchart illustrating a method of controlling a biomaterial test apparatus according to an embodiment of the present invention.

FIG. 9 is a flowchart illustrating a method of controlling a biomaterial test apparatus according to an embodiment of the present invention.

First, the air temperature $t_0$ in the vicinity of the platform receiving chamber 160 is identified. Here, the air temperature in the vicinity of the platform receiving chamber 160 means a temperature of air present outside the platform receiving chamber 160 in air inside the housing 101. That is, the air temperature of an environment in which the platform receiving chamber 160 to perform the biomaterial test is placed is identified to determine whether to proceed with the biomaterial test.

The identified air temperature $t_0$ may be compared with the first critical temperature $t_L$. Here, the first critical temperature means the lowest temperature at which the biomaterial test apparatus is operated. It is difficult to normally perform the biomaterial test at a temperature below the first critical temperature. Accordingly, in order to prevent waste of unnecessary power and time, the air temperature $t_0$ may be compared with the first critical temperature $t_L$, prior to testing.

The first critical temperature $t_L$ may be input through the input portion by a tester or may also be determined by calculation within the biomaterial test apparatus.

As a result of comparing the air temperature $t_0$ with the first critical temperature $t_L$, when the air temperature $t_0$ is less than the first critical temperature $t_L$, the biomaterial test may not proceed. Accordingly, the display 103 may display the screen indicating that the biomaterial test is inoperative. This may previously prevent unnecessary test progress, thereby preventing waste of power and time.

It may be possible to inform an external tester that the test is impracticable through the display 103 and block the operation of the heater 161 which heats the inside of the platform receiving chamber 160. Consequently, it may be possible to block the unnecessary operation of the heater 161 and thus lifespan of the heater 161 may be extended.

Meanwhile, as a result of comparing the air temperature $t_0$ with the first critical temperature $t_L$, when the air temperature $t_0$ is equal to or more than the first critical temperature $t_L$, the biomaterial test may proceed. A detailed description thereof will be given with reference to FIG. 10.

Figure 10:
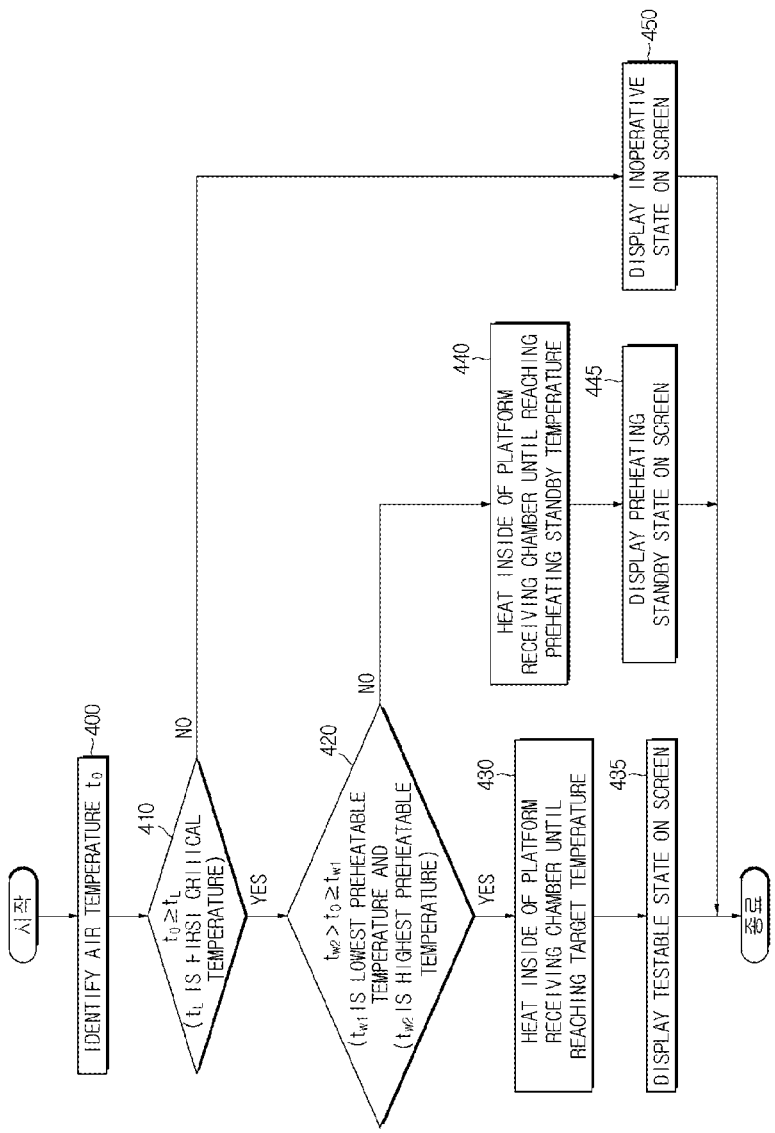
FIG. 10 is a flowchart illustrating a method of controlling a biomaterial test apparatus according to another embodiment of the present invention.

FIG. 10 is a flowchart illustrating a method of controlling a biomaterial test apparatus according to another embodiment of the present invention.

First, the air temperature $t_0$ in the vicinity of the platform receiving chamber 160 is identified. Similarly to FIG. 9, the air temperature in the vicinity of the platform receiving chamber 160 may mean a temperature of air present outside the platform receiving chamber 160 in air inside the housing 101.

The identified air temperature $t_0$ may be compared with the first critical temperature $t_L$. Since the biomaterial test may not proceed when the air temperature $t_0$ is less than the first critical temperature $t_L$, it may be possible to inform an external tester that the biomaterial test is impracticable through the display 103.

Meanwhile, when the air temperature $t_0$ is equal to or more than the first critical temperature $t_L$, the biomaterial test may proceed. First, it is determined whether the air temperature $t_0$ is present in a preheatable range, namely, is present between the lowest preheatable temperature $t_{W1}$ and the highest preheatable temperature $t_{W2}$.

Here, the preheatable range means an air temperature range in which the inside of the platform receiving chamber 160 is heated to reach a desired target temperature. When the air temperature $t_0$ is present in the preheatable range, the progress of preheating is useful. However, when the air temperature $t_0$ is not present in the preheatable range, the inside of the platform receiving chamber 160 may not reach the target temperature even when preheating is performed. Therefore, it is first determined whether the air temperature $t_0$ is present in the preheatable range.

If the air temperature $t_0$ is present in a non-preheating range instead of the preheatable range, the inside of the platform receiving chamber 160 may not reach the target temperature. In this case, the inside of the platform receiving chamber 160 may be heated until reaching a preheating standby temperature without being unnecessarily heated to reach the target temperature. The preheating standby temperature means a temperature of the platform receiving chamber 160 set such that preheating is performed according to a change in air temperature for the future when the air temperature is present in the non-preheating range. When the temperature of the platform receiving chamber 160 reaches the preheating standby temperature, the biomaterial test apparatus may be in a preheating standby state.

When the temperature of the platform receiving chamber 160 reaches the preheating standby temperature by heating the inside of the platform receiving chamber 160, the display 103 may display a screen indicating that the biomaterial test apparatus is in the preheating standby state. The external tester may identify the state of the biomaterial test apparatus through the display 103 and move the biomaterial test apparatus to a proper environment so as to again perform the test.

If the air temperature $t_0$ is present in the preheatable range instead of the non-preheating range, the inside of the platform receiving chamber 160 may be heated until reaching a target temperature. The target temperature means an optimal temperature of the platform receiving chamber 160 for the biomaterial test, and may be input by a tester or determined by calculation within the apparatus.

While the inside of the platform receiving chamber 160 may be heated until reaching a target temperature, the display 103 may display a screen indicating a preheating progress state. When the tester identifies the screen, the biomaterial test may be previously prepared to be performed by the tester.

When the inside of the platform receiving chamber 160 is heated and reaches the target temperature, the display 103 may display a testable state on the screen. When the inside of the platform receiving chamber 160 reaches the target temperature as an optimal temperature for the biomaterial test, there is a need to inform an external tester that the biomaterial test is prepared to begin. The external tester may identify that the biomaterial test apparatus is in the testable state through the display 103 and then proceed with the biomaterial test through the input.

The method of controlling a biomaterial test apparatus can also be embodied as computer readable codes on a computer readable recording medium. The computer readable recording medium includes any data storage device that can store data which can be thereafter read by a computer system. Examples of the computer readable recording medium include ROM, RAM, CD-ROMs, magnetic tapes, floppy disks, optical data storage devices, and the like. In addition, the computer readable recording medium can be distributed over network coupled computer systems so that the computer readable code is stored and executed in a distributed fashion.

Various embodiments have been described in the best mode for carrying out the invention. Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A biomaterial test apparatus comprising:
   a housing;
   a platform receiving chamber arranged inside the housing and capable of receiving a platform into which a biomaterial is injected;
   a display which is arranged outside the housing and displays a control screen to test the biomaterial;
   a temperature sensor which senses a temperature of the platform receiving chamber and an air temperature in the vicinity thereof; and
   a control unit which, when the air temperature is less than a predetermined first critical temperature, controls the display so as to display a screen indicating that the test is impracticable,
   wherein the platform receiving chamber comprises a heater which heats the inside of the Platform receiving chamber; and
   when the air temperature is equal to or more than the first critical temperature, the control unit is configured to:

determine whether the air temperature is present within a predetermined preheatable range, or a predetermined non-preheating range; and control the heater such that the inside of the platform receiving chamber is heated based on whether the air temperature is within the predetermined preheatable range, or the predetermined non-preheating range.

2. The biomaterial test apparatus according to claim 1, wherein the air temperature is an air temperature outside the platform receiving chamber within the housing.

3. The biomaterial test apparatus according to claim 1, wherein:

when the air temperature is less than the first critical temperature, the control unit is configured to terminate driving of the heater.

4. The biomaterial test apparatus according to claim 1, wherein when the air temperature is present within the predetermined non-preheating range, the control unit is configured to operate the heater until a temperature of the platform receiving chamber reaches a predetermined preheating standby temperature.

5. The biomaterial test apparatus according to claim 4, wherein when the temperature of the platform receiving chamber reaches the preheating standby temperature by the heater, the display displays a screen indicating that the test apparatus is in a preheating standby state.

6. The biomaterial test apparatus according to claim 1, wherein when the air temperature is present within the predetermined preheatable range, the control unit is configured to operate the heater until a temperature of the platform receiving chamber reaches a predetermined target temperature.

7. The biomaterial test apparatus according to claim 6, wherein:

the display displays a screen indicating that the test apparatus is in a preheating progress state during operation of the heater; and when the temperature of the platform receiving chamber reaches the target temperature by the heater, the display displays a screen indicating that the test apparatus is in a preheating completion state or a testable state.

8. The biomaterial test apparatus according to claim 1, wherein the platform receiving chamber comprises a cooler to cool the inside of the platform receiving chamber.

9. The biomaterial test apparatus according to claim 8, wherein when the air temperature exceeds a predetermined second critical temperature, the control unit is configured to control cooler so as to cool the inside of the platform receiving chamber.

10. A method of controlling a biomaterial test apparatus, comprising:

identifying a temperature in a platform receiving chamber and an air temperature in the vicinity thereof;

comparing the air temperature with a predetermined first critical temperature;

displaying that a biomaterial test apparatus is impracticable on a display screen when the air temperature is less than a predetermined first critical temperature;

determining, when the air temperature is equal to or more than the first critical temperature, whether the air temperature is present within a predetermined preheatable range or a predetermined non-preheating range; and heating the inside of the platform receiving chamber based on a result of the determining.

11. The method according to claim 10, wherein the air temperature is an air temperature outside the platform receiving chamber within a housing.

12. The method according to claim 10, further comprising, when the air temperature is less than the predetermined first critical temperature, blocking driving of a heater which heats the inside of the platform receiving chamber.

13. The method according to claim 10, wherein when the air temperature is present in the non-preheating range, the inside of the platform receiving chamber is heated until reaching a predetermined preheating standby temperature.

14. The method according to claim 13, further comprising, when the inside of the platform receiving chamber is heated and reaches the preheating standby temperature, displaying that the biomaterial test apparatus is in a preheating standby state on the display screen.

15. The method according to claim 10, wherein when the air temperature is present in the preheatable range, the inside of the platform receiving chamber is heated until reaching a target temperature.

16. The method according to claim 15, further comprising:

displaying that the biomaterial test apparatus is in a preheating progress state on the display screen during heating of the platform receiving chamber; and displaying that the biomaterial test apparatus is in a preheating completion state or a testable state on the screen when the platform receiving chamber reaches the target temperature.

17. The method according to claim 10, further comprising:

comparing the air temperature with a predetermined second critical temperature; and cooling the platform receiving chamber when the air temperature exceeds the second critical temperature, wherein the second critical temperature is higher than the first critical temperature.

18. The method according to claim 10, wherein the platform receiving chamber is arranged inside a housing of the biomaterial test apparatus and a platform into which a biomaterial is injected is inserted into the platform receiving chamber.

* * * * *